United States Patent
Nygaard

(10) Patent No.: US 7,312,607 B2
(45) Date of Patent: Dec. 25, 2007

(54) EDDY CURRENT PART INSPECTION SYSTEM

(75) Inventor: George Nygaard, Davisburg, MI (US)

(73) Assignee: General Inspection LLC, Davisburg, MI (US)

( * ) Notice: Subject to any disclaimer, the term of this patent is extended or adjusted under 35 U.S.C. 154(b) by 151 days.

(21) Appl. No.: 11/161,045

(22) Filed: Jul. 20, 2005

(65) Prior Publication Data

US 2006/0022669 A1 Feb. 2, 2006

Related U.S. Application Data

(60) Provisional application No. 60/521,915, filed on Jul. 20, 2004.

(51) Int. Cl.
*G01N 27/72* (2006.01)
*G01N 27/82* (2006.01)

(52) U.S. Cl. ..................... 324/228; 324/238

(58) Field of Classification Search ............. 324/228, 324/232, 237–240
See application file for complete search history.

(56) References Cited

U.S. PATENT DOCUMENTS

| | | | |
|---|---|---|---|
| 3,146,395 A | 8/1964 | Quittner | 324/37 |
| 3,500,181 A | 3/1970 | Jackson | 324/37 |
| 3,518,533 A | 6/1970 | Arnelo | 324/40 |
| 3,731,184 A | 5/1973 | Goldberg et al. | 324/34 R |
| 3,936,733 A | 2/1976 | Clary | 324/34 R |
| 3,940,690 A | 2/1976 | Suhr et al. | 324/37 |
| 4,351,184 A | 9/1982 | Garner et al. | 73/104 |
| 4,480,225 A | 10/1984 | Nance et al. | 324/238 |
| 4,507,610 A | 3/1985 | Nakaoka | 324/238 |
| 4,630,229 A | 12/1986 | D'Hondt | 364/726 |
| 4,659,990 A | 4/1987 | Tore | 324/238 |
| 4,719,422 A | 1/1988 | deWalle et al. | 324/238 |
| 4,829,247 A | 5/1989 | Wallrafen | 324/208 |
| 4,893,077 A | 1/1990 | Auchterlonie | 324/208 |
| 4,906,927 A | 3/1990 | Urata et al. | 324/238 |
| 5,041,786 A | 8/1991 | Takaishi et al. | 324/240 |
| 5,412,319 A | 5/1995 | Ciani | 324/241 |
| 5,559,431 A | 9/1996 | Sellen | 324/202 |
| 5,638,000 A | 6/1997 | Forster | 324/238 |
| 5,895,439 A | 4/1999 | Fisher et al. | 702/36 |
| 6,005,392 A | 12/1999 | Patzwaldt | 324/329 |
| 6,288,536 B1 | 9/2001 | Mandl et al. | 324/225 |
| 2004/0075429 A1 | 4/2004 | Hiroshima | 324/242 |

OTHER PUBLICATIONS technical paper eddyc.pdf downloaded from the internet at http://joe.buckley.net/papers on Sep. 8, 2003, 7 pp.
Internet web pages at http://www.ndt-ed.org/EducationResources/CommunityCollege/EddyCurrents/cc_ec_index.htm, downloaded on Jun. 17, 2004, and Oct. 13, 2005, 118 pp.

*Primary Examiner*—Bot LeDynh
(74) *Attorney, Agent, or Firm*—Brooks Kushman P.C.

(57) ABSTRACT

At least one measurement coil of an eddy current part inspection system is oriented relative to a track surface so that the longitudinal axis of the magnetic field generated by the at least one measurement coil is skewed relative to the track surface so as to be substantially aligned with the longitudinal axis of a part on the track surface which can move thereon through the at least one measurement coil.

26 Claims, 13 Drawing Sheets

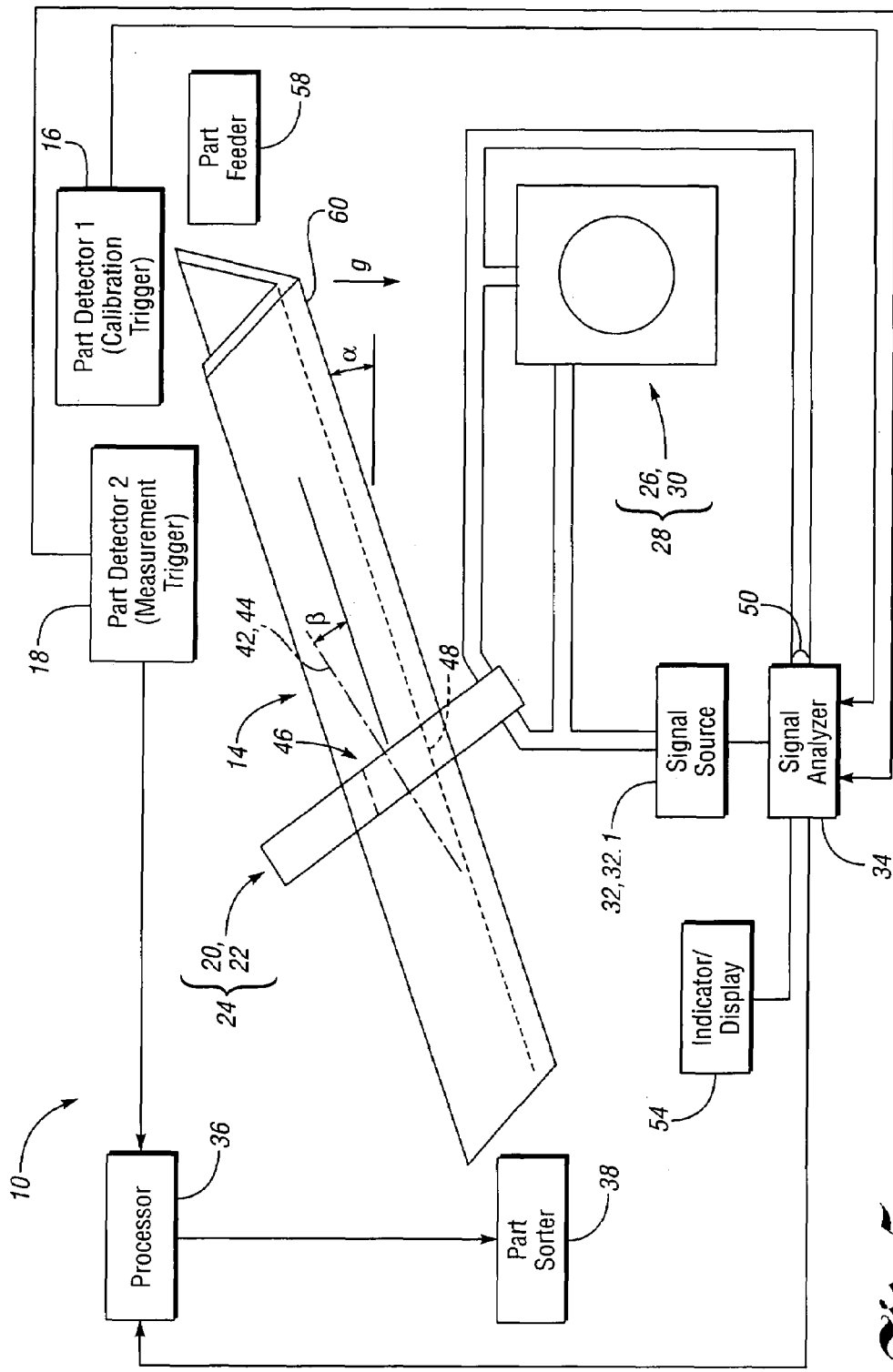

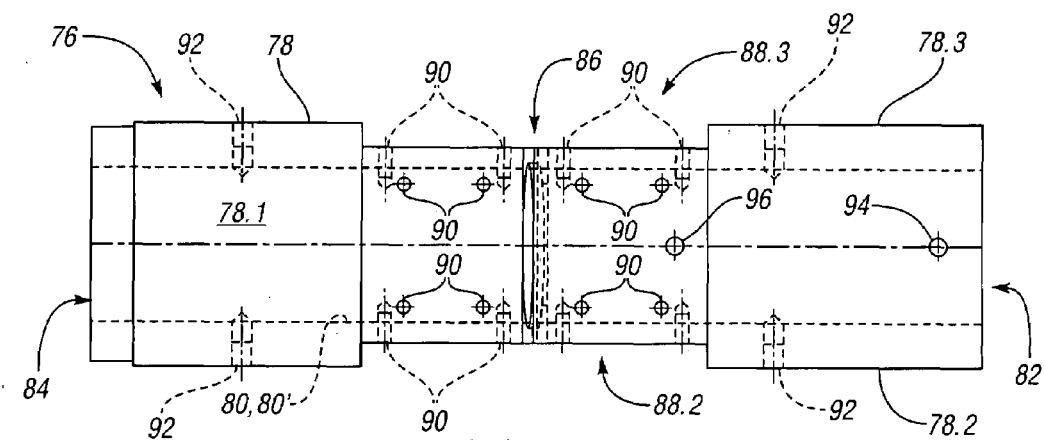
Fig. 10a
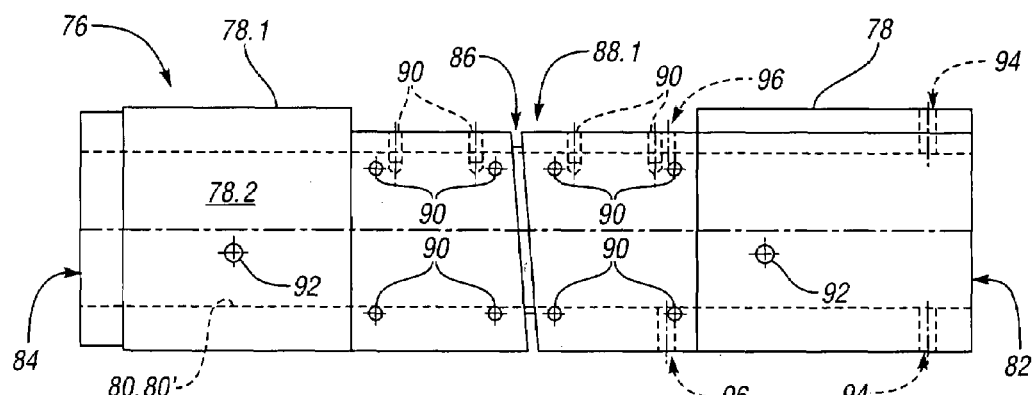
Fig. 10b
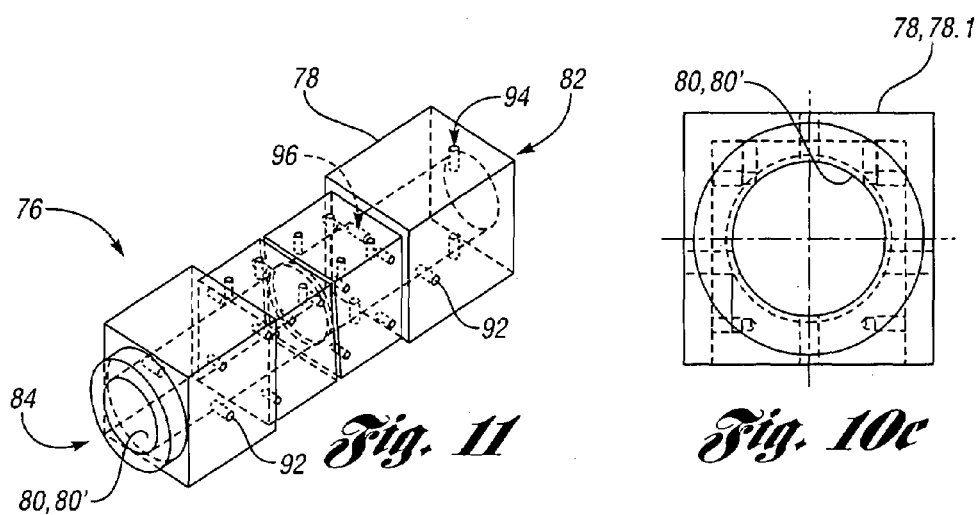
Fig. 11
Fig. 10c

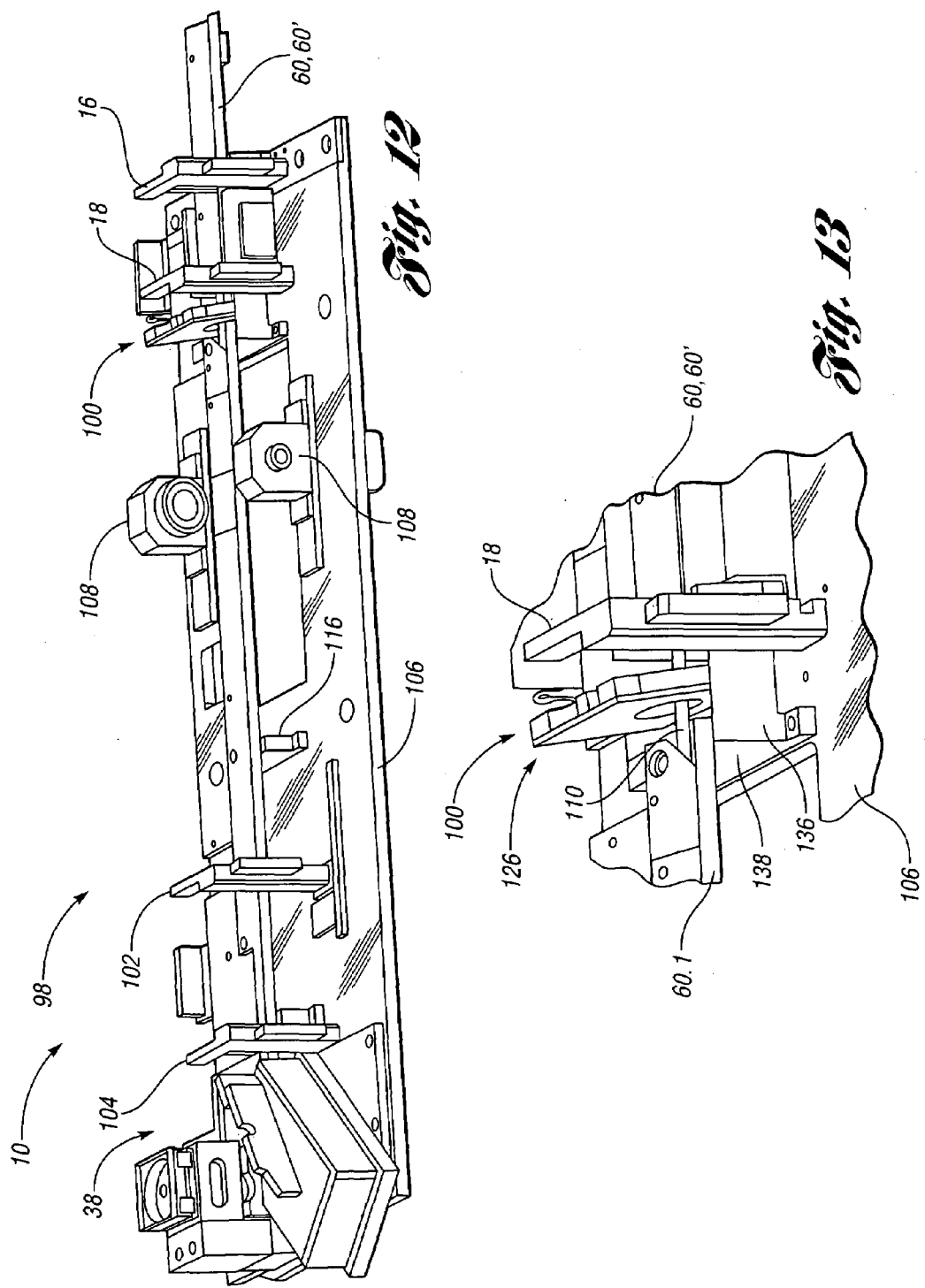

EDDY CURRENT PART INSPECTION SYSTEM

CROSS-REFERENCE TO RELATED APPLICATIONS

The instant application claims the benefit of prior U.S. Provisional Application Ser. No. 60/521,915 filed on Jul. 20, 2004, which is incorporated herein by reference.

BRIEF DESCRIPTION OF THE DRAWINGS

In the accompanying drawings: privilege

FIG. 5 illustrates another embodiment of an eddy current part inspection system;

FIG. 10a illustrates a top view of a portion of a track that provides for integration of a coil assembly therewith;

FIG. 10b illustrates a side view of the track portion illustrated in FIG. 10a;

FIG. 10c illustrates an end view of the track portion illustrated in FIGS. 10a-b;

FIG. 11 illustrates an isometric view of the track portion illustrated in FIGS. 10a-c;

FIG. 12 illustrates an isometric view of a physical embodiment of track and sensor assembly of an eddy current part inspection system;

FIG. 13 illustrates a portion of the eddy current part inspection system illustrated in FIG. 12, including the eddy current sensor assembly and portions of the track and sensor assembly proximate thereto;

FIG. 18b illustrates a side view of the eddy current sensor assembly and associated stanchion and support plates illustrated in FIG. 18a;

FIG. 19b illustrates a side view of the reference coil assembly and associated magnetic bias adjustment assembly illustrated in FIG. 19a.

DETAILED DESCRIPTION OF EMBODIMENT(S)

Figure 1:
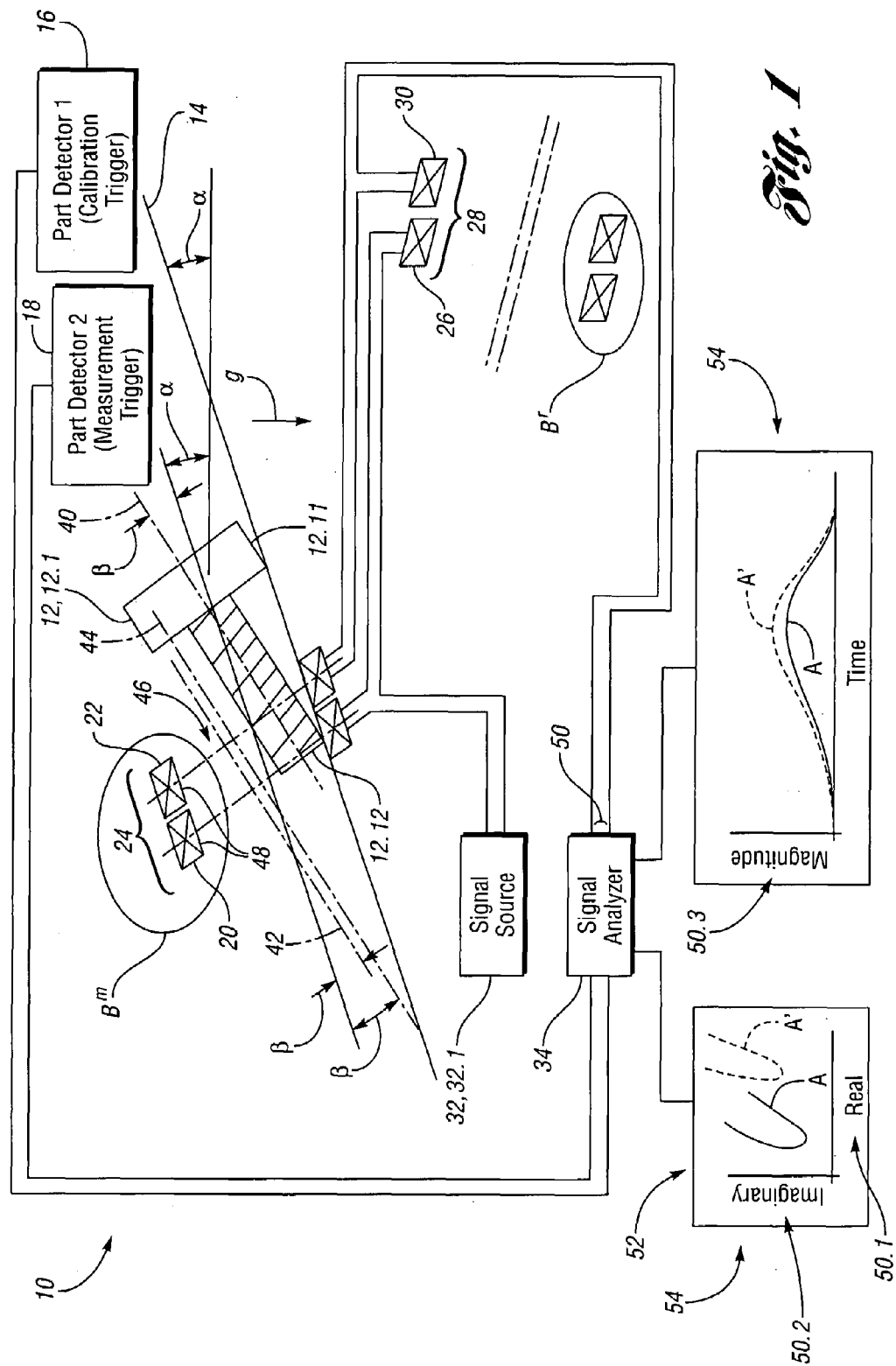
FIG. 1 illustrates an embodiment of an eddy current part inspection system.
Figure 2:
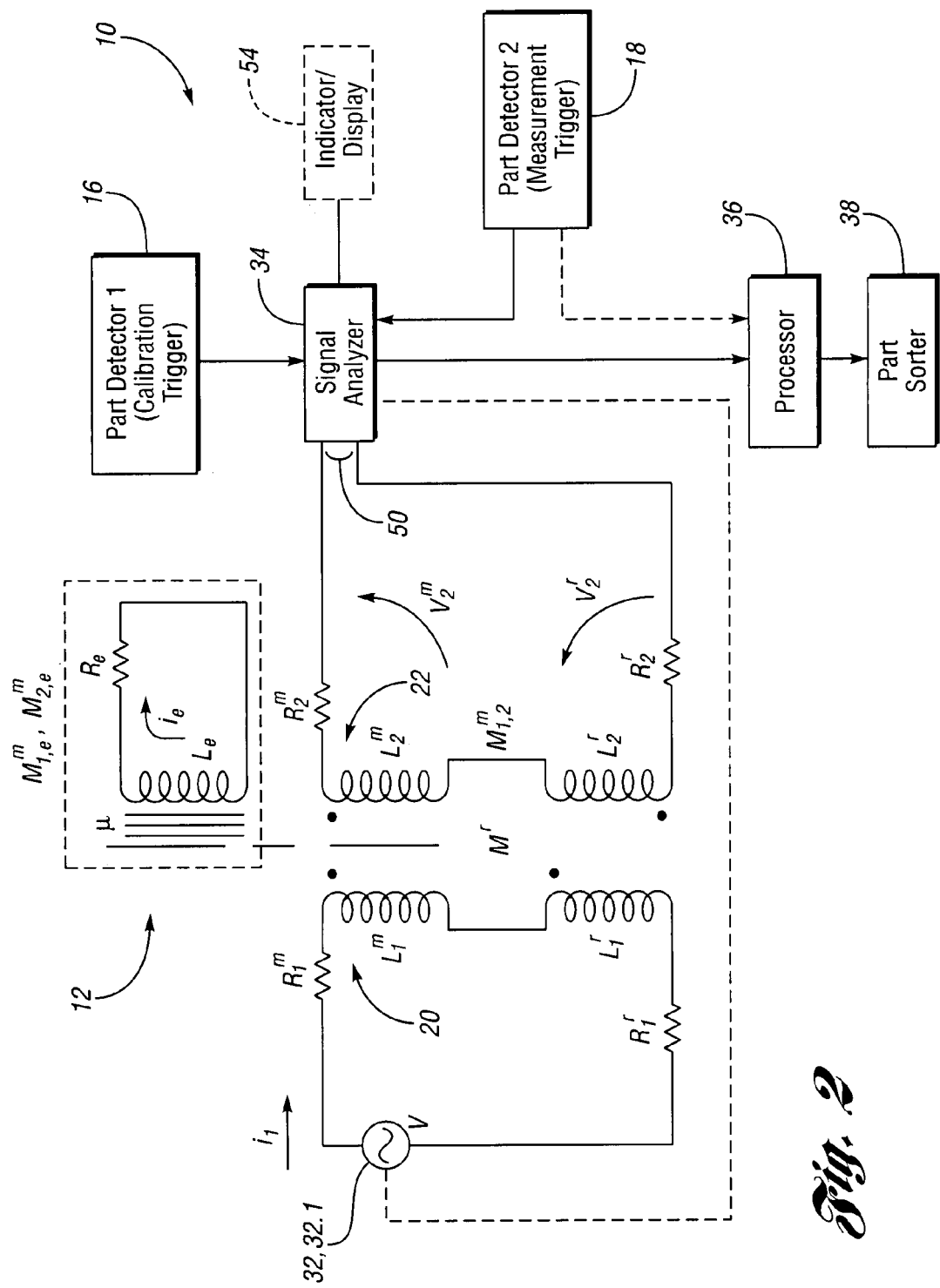
FIG. 2 illustrates a combined schematic and block diagram of the eddy current part inspection system illustrated in FIG. 1.

Referring to FIGS. 1 and 2, in an eddy current part inspection system 10, a part 12 to be inspected, e.g. a bolt 12.1, slides responsive to a gravitational acceleration field g along a track surface 14 tilted at an angle α from horizontal. After sliding past a first part detector 16 and then a second part detector 18, the part 12 slides through first 20 and second 22 coils of a measurement coil pair 24. As the part 12 slides along the track surface 14, each point in the part follows a trajectory, which for example, would be parallel to the track surface 14. For example, the first 16 and second 18 part detectors may comprise respective light beams that are generated by respective light emitting diodes, and detected by associated respective photodetectors, wherein a part 12 passing through the light beam occludes the light beam, which is detected by the photodetector. The first coil 20 of the measurement coil pair 24 is connected in series with a first coil 26 of a reference coil pair 28, and the second coil 22 of the measurement coil pair 24 is connected in series with a second coil 30 of the reference coil pair 28, wherein the relative polarity of the first 20 and second 22 coils of the measurement coil pair 24 is opposite to the relative polarity of the first 26 and second 30 coils of the reference coil pair 28. A signal source 32, for example, a sinusoidal oscillator 32.1, for example, adapted to operate at a frequency between 1 and 300 KHz, is connected in series with the first coils 20, 26 of the measurement 24 and reference 28 coil pairs. The series combination of the second coils 22, 30 of the measurement 24 and reference 28 coil pairs is connected to a signal analyzer 34, which is also operatively coupled to the first 16 and second 18 part detectors, and to a processor 36 that controls a part sorter 38 operatively coupled thereto.

The part 12 is shaped so that, when sliding on the track surface 14, the longitudinal axis 40 of the part 12 is skewed at an angle β relative to the track surface 14, and to the trajectory followed by the part 12. For example, the relatively larger diameter of the head 12.11 relative to the shank 12.12 of a bolt 12.1 causes the longitudinal axis 40 of the bolt 12.1 supported on the track surface 14 by the head 12.11 and the shank 12.12 to be skewed relative to the track surface 14. The longitudinal magnetic field axes 42, 44 of the first 20 and second 22 coils of the measurement coil pair 24 are aligned parallel to one another, and are both skewed at the angle β relative to the track surface 14, so that the longitudinal axis 40 of a part 12 sliding through the first 20 and second 22 coils of the measurement coil pair 24 is substantially parallel to the longitudinal magnetic field axes 42, 44 of the first 20 and second 22 coils. In one embodiment, the first 20 and second 22 coils of the measurement coil pair 24 are shaped so that the openings thereof substantially conform to and provide clearance for the part 12 sliding therethrough along the track surface 14, so as to maximize the percentage of core area 46 of the first 20 and second 22 coils that is filled by the part 12 as the part 12 slides therethrough. For example, in the embodiment illustrated in FIG. 1, the longitudinal magnetic field axes 42, 44 of the first 20 and second 22 coils of the measurement coil pair 24 are offset with respect to one another so that the core profile 48 is relatively uniform with respect to the part 12 as the part 12 slides therethrough. Alternatively, the first 20 and second 22 coils of the measurement coil pair 24 could be co-wound on a common coil form, for example, by interlacing the windings of the first 20 and second 22 coils thereon.

The first 26 and second 30 coils of the reference coil pair 28 are substantially aligned with one another and are substantially isolated from the part 12, so as to not be magnetically influenced thereby. For example, in the embodiment illustrated in FIG. 1, the first 26 and second 30 coils of the reference coil pair 28 are substantially the same type, and in the same relative orientation, as the first 20 and second 22 coils of the measurement coil pair 24.

Referring to FIG. 2, the first 20 and second 22 coils of the measurement coil pair 24 are each modeled by the combination of a respective resistance $R_1^m$, $R_2^m$ in series with an associated respective inductance $L_1^m$, $L_2^m$ respectively, and are magnetically coupled by their relatively close proximity to one another so as to exhibit a mutual inductance $M_{1,2}^m$. Similarly, the first 26 and second 30 coils of the reference coil pair 28 are each modeled by the combination of a respective resistance $R_1^r$, $R_2^r$ respectively in series with an associated respective inductance $L_1^r$, $L_2^r$, and are magnetically coupled by their relatively close proximity to one another so as to exhibit a mutual inductance $M^r$. An oscillatory voltage v applied by the signal source 32 to the series combination of the first coils 20, 26 of the measurement 24 and reference 28 coil pairs generates a corresponding oscillatory current $i_1$, in the first coils 20, 26, which generates a corresponding oscillatory magnetic flux $B^m$, $B^r$ in the respective first coils 20, 26, which generates associated oscillatory voltages $v_2^m$, $v_2^r$ across the respective second coils 22, 30 of the measurement 24 and reference 28 coil pairs in accordance with the associated mutual inductances $M_{1,2}^m$, $M^r$. The signal 50—i.e. the sum of the oscillatory voltages $v_2^m$, $v_2^r$—generated from the series combination of the second coils 22, 30 of the measurement 24 and reference 28 coil pairs is analyzed by the signal analyzer 34, which, for example, analyzes the signal 50 in the complex plane 52, for example, by plotting the real 50.1 and imaginary 50.2 components of the signal 50 in the complex plane 52, wherein the real component 50.1 is in-phase with the signal source 32—i.e. with the oscillatory voltage v thereof—and the imaginary component 50.2 is ninety degrees out-of-phase with the signal source 32. The decomposition of the signal 50 into corresponding real 50.1 and imaginary 50.2 components is well known in the art, and may be accomplished using analog circuitry, digital circuitry or by software or a combination thereof. For example, U.S. Pat. Nos. 4,630,229, 6,005,392 and 6,288,536—all of which is incorporated by reference herein in their entirety—each disclose various systems and methods for calculating in real-time the real 50.1 and imaginary 50.2 components of a signal 50. A Maxwell-Wien bridge may also be used to determine the real 50.1 and imaginary 50.2 components of the signal 50, or a phase-locked loop may be used to determine the relative phase of the signal 50 with respect to the signal source 32, which then provides for determining the associated real 50.1 and imaginary 50.2 components. Generally, the signal analyzer 34 alternatively could use phase only, amplitude only, or other complex impedance plane methods to analyze the signal 50. The signal analyzer 34 may also provide for plotting of the magnitude 50.3 of the signal 50 as a function of time. In one embodiment, the real 50.1 and imaginary 50.2 components of the signal 50 are plotted in the complex plane 52 over time and displayed on an indicator or display device 54, as is the magnitude 50.3 of the signal 50 as a function of time.

Figure 3A:
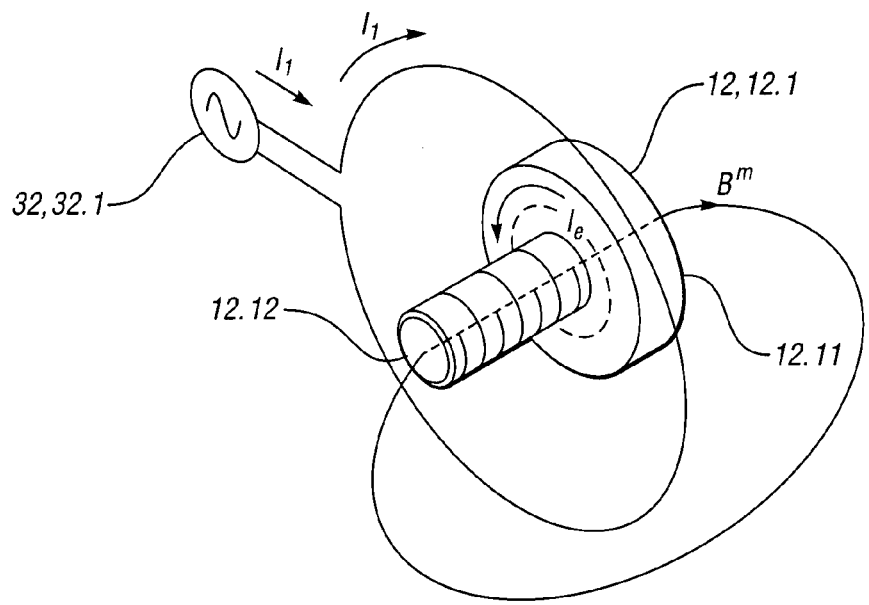
FIG. 3a illustrates the coil current, associated magnetic flux, and eddy current for a non-defective part.
Figure 3B:
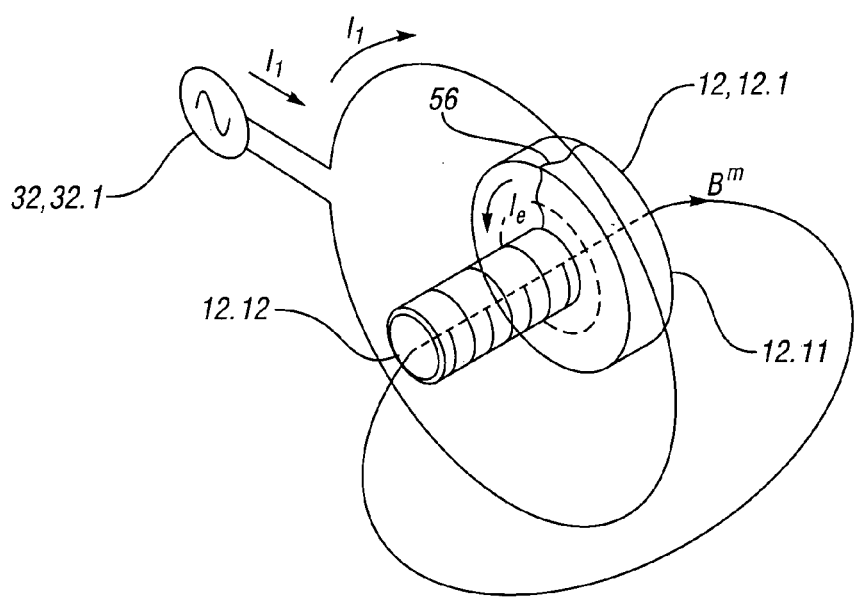
FIG. 3b illustrates the coil current, associated magnetic flux, and eddy current for a defective part.

In a quiescent state—absent a part 12 affecting the magnetic circuit of the first 20 and second 22 coils of the measurement coil pair 24—the oscillatory voltages $v_2^m$, $v_2^r$ from the second coils 22, 30 of the measurement 24 and reference 28 coil pairs are of similar magnitude and opposite phase, thereby substantially canceling one another so that the composite signal 50 is substantially null. Under these conditions, the signal analyzer 34 may be calibrated to remove any residual offset in the associated composite signal 50. The presence of a part 12 in proximity to the measurement coil pair 24 affects that magnetic circuit, which in turn affects the oscillatory voltage $v_2^m$, thereby perturbing the signal 50 responsive to the extent to which the part 12 perturbs the magnetic circuit of the measurement coil pair 24. For example, the part 12 may exhibit a permeability μ which affects magnetic coupling between the first 26 and second 30 coils of the measurement coil pair 24. Referring to FIGS. 3a and 3b, if the part 12 is conductive, then the oscillatory magnetic flux $B^m$ generated by the oscillatory current $i_1$ in the first coil 20 generates an eddy current $i_e$ in the part 12, wherein, in accordance with Lenz's law, the direction of the eddy current $i_e$ is such that the magnetic flux generated thereby opposes that oscillatory magnetic flux $B^m$ generating the eddy current $i_e$, or in other words, the direction of the eddy current $i_e$ is opposite to that of the oscillatory current $i_1$ in the first coil 20. Referring to FIG. 3b, a fracture or crack 56 in the part 12 across the path of the eddy current $i_e$ increases the resistance to the eddy current $i_e$, thereby decreasing the magnitude of the eddy current $i_e$ and the corresponding magnitude of the associated eddy current magnetic field component, so that the net magnetic field affecting the second coil 22 of the measurement coil pair 24 is greater than for a part 12 without a fracture or crack 56 for which the eddy current $i_e$ and the corresponding magnitude of the associated eddy current magnetic field component—opposing the oscillatory magnetic flux $B^m$—are relatively greater. Referring to FIG. 2, the affect of the part 12 on the oscillatory magnetic flux $B^m$ is modeled as an associated inductance $L_e$, and the net resistance of the part 12 along the path of the eddy current $i_e$ is modeled as lumped resistance $R_e$. An increase in resistance $R_e$ as a result of a fracture or crack 56 is indicated by increases in the real 50.1 and imaginary 50.2 components of the signal 50 from the second coils 22, 30 of the measurement 24 and reference 28 coil pairs, as indicated in FIG. 1 by point A' relative to point A in both the complex plane 52 and the plot of the associated magnitude 50.3 of the signal 50 as a function of time. The sensitivity of the eddy current $i_e$ to the fracture or crack 56, particularly a radial plane fracture or crack 56.1, is enhanced by orienting the oscillatory magnetic flux $B^m$ with the longitudinal axis 40 of the part 12, as is provided by the arrangement of the longitudinal magnetic field axes 42, 44 aligned with the longitudinal axis 40 of the part 12 and oblique to the track surface 14, as illustrated in FIG. 1.

Figure 4:
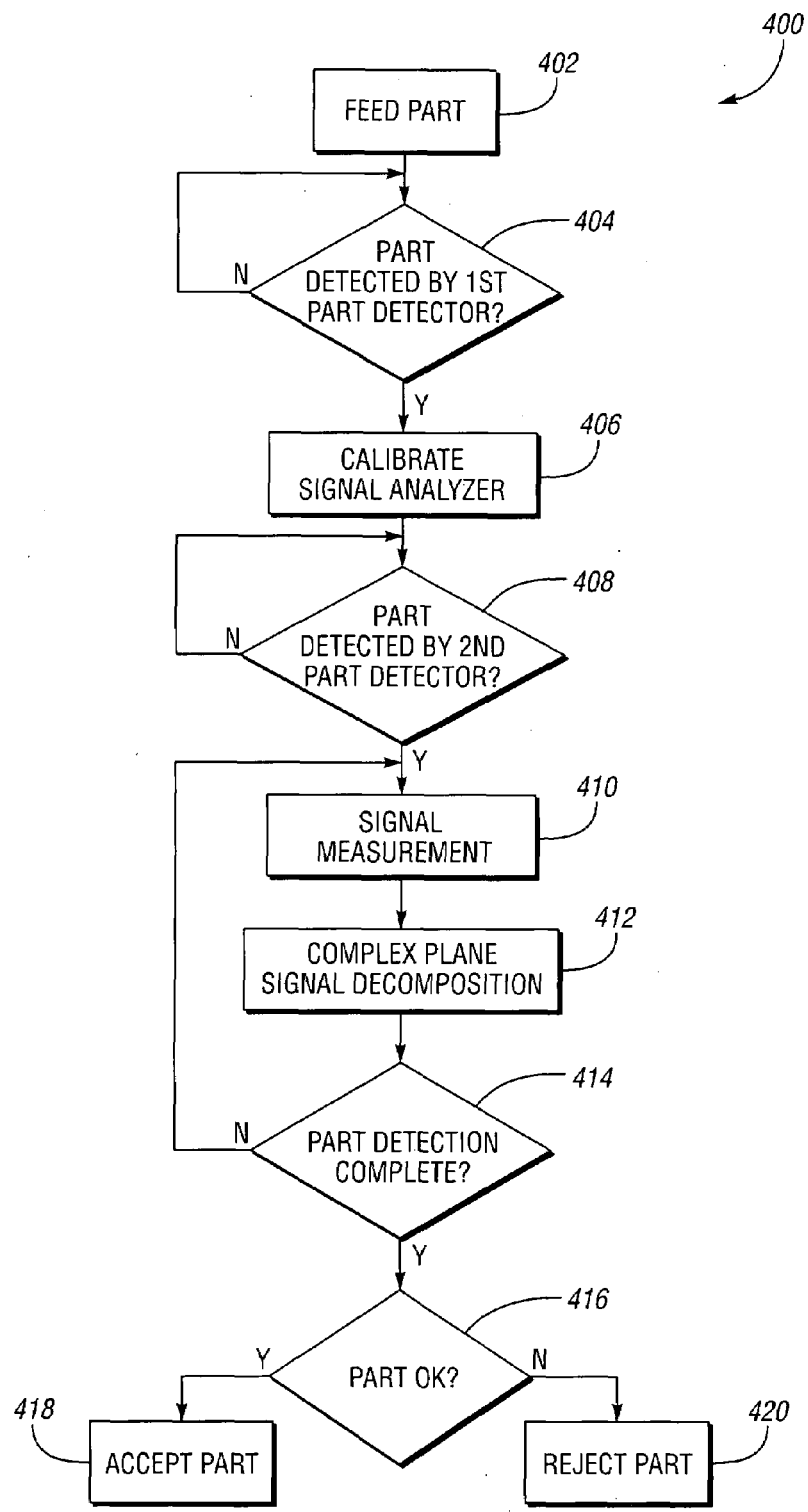
FIG. 4 illustrates a flowchart of an eddy current part inspection process.

Referring also to FIGS. 4 and 5, an eddy current part inspection process 400 commences in step (402), wherein parts 12 are fed, e.g. asynchronously, one at a time from an automatic part feeder 58 onto a track 60. For example, in one embodiment, the track 60 comprises V-shaped trough constructed from a non-magnetic material—for example, an ultra-high molecular weight plastic—particularly in proximity to the measurement coil pair 24. The parts 12 slide down the track 60, which is tilted at an angle α with respect to the gravitational acceleration field g so as to provide for automatic movement of parts therealong. In step (404), when a part 12 is detected by the first part detector 16, then in step (406), the signal analyzer 34 is triggered to calibrate the measurement coil pair 24 before the part 24 becomes proximate thereto, whereby the signal analyzer 34 compensates for any bias in the combined signal 50 from the second coils 22, 30 of the measurement 24 and reference 28 coil pairs, so as to null the combined signal 50. Then, in step (408), when a part 12 is detected by the second part detector 18, then, in step (410), the signal analyzer 34 is triggered to commence making repetitive measurements of the combined signal 50 from the second coils 22, 30 of the measurement 24 and reference 28 coil pairs. In step (412), the signal 50 is decomposed in the real 50.1 and imaginary 50.2 components. If, in step (414), the part detection process is not complete, then the process repeats with step (410). Otherwise, in step (416), if a complex plane analysis of the composite results from step (412) indicates that the part 12 is acceptable, then in step (418), the processor 36 controls the part sorter 38 to accept the part 12. Otherwise, from step (416), if a complex plane analysis of the composite results from step (412) indicates that the part 12 is not acceptable, then in step (420), the processor 36 controls the part sorter 38 to reject the part 12. In one embodiment, the signal analyzer 34 measures and decomposes the signal 50 into real 50.1 and imaginary 50.2 components in steps (410) and (414) and discriminates the results in step (416), and then communicates the result to the processor 36. In another embodiment, the signal analyzer 34 communicates the results from step (412) to the processor 36, which then carries out the discrimination process of step (416). In yet another embodiment, the signal analyzer 34 and processor 36 are combined. The signal analyzer 34 and processor 36 are typically implemented with one or more computers or digital signal processors, but generally could be implemented with either analog or digital electronic circuitry.

Figure 6A:
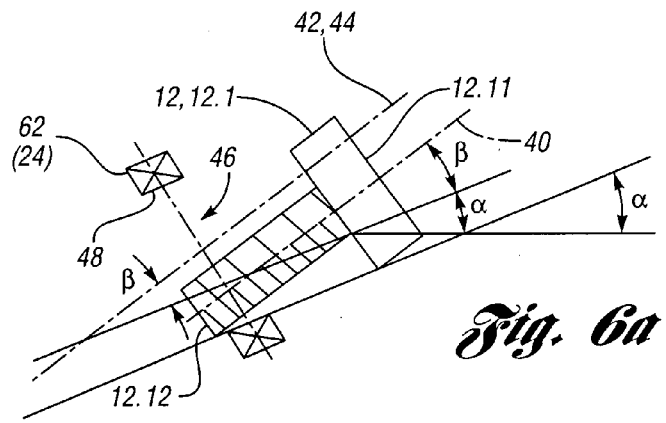
FIG. 6a illustrates an embodiment of a measurement coil of an eddy current part inspection system.
Figure 6B:
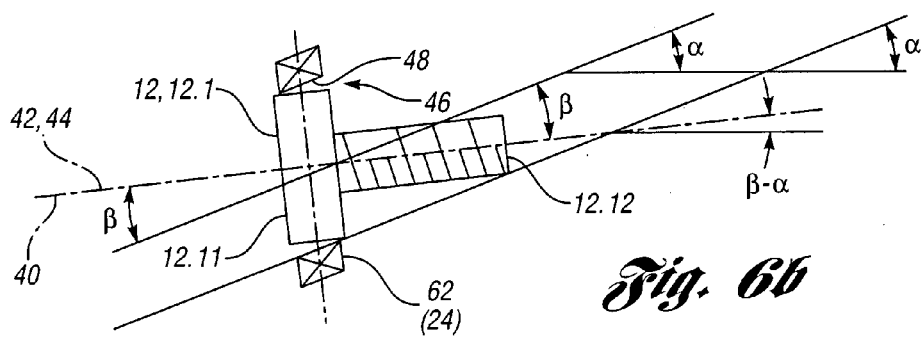
FIG. 6b illustrates another embodiment of a measurement coil of an eddy current part inspection system.
Figure 7:
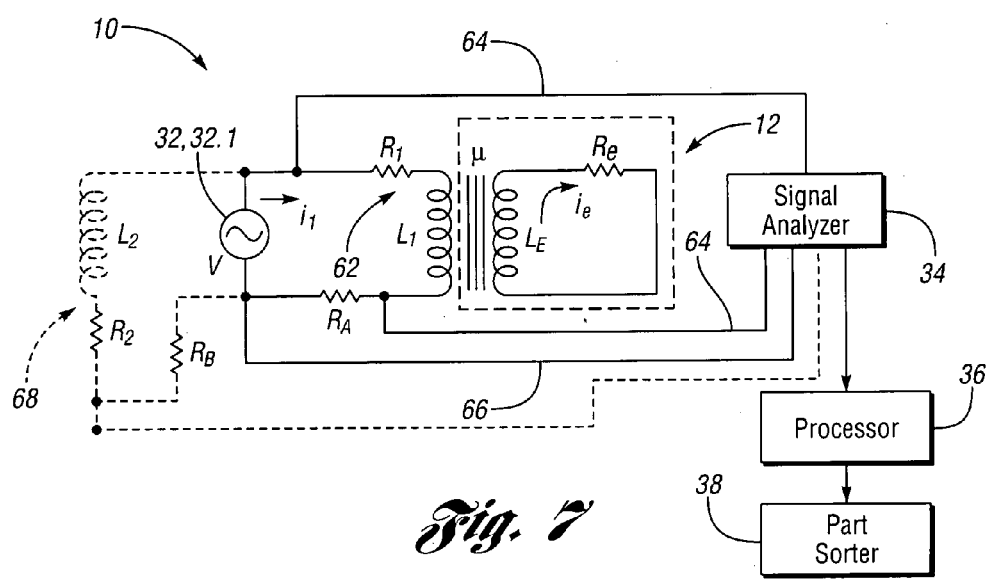
FIG. 7 illustrates a combined schematic and block diagram of and eddy current part inspection system incorporating a single measurement coil.

Referring to FIGS. 6a and 6b, the eddy current part inspection system 10 can be adapted to use a single measurement coil 62 to both generate the oscillatory magnetic flux $B'''$, and to generate a self-inductance signal responsive to the part 12. Referring to FIG. 7, in one embodiment, the signal source 32, e.g. a sinusoidal oscillator 32.1, is connected to the series combination of the measurement coil 62 and a sense resistor $R_A$, wherein the measurement coil 62 is represented by an inductance $L_1$ in series with an associated inductance $R_1$. The signal analyzer 34 measures a signal 64 across the measurement coil 62, and measures a reference signal 66, i.e. either the oscillatory voltage v of the signal source 32 or the voltage across the sense resistor $R_A$ which provides a measure of the oscillatory current $i_1$ through the measurement coil 62. The signal analyzer 34 decomposes the signal 64 from the measurement coil 62 into real 50.1 and imaginary 50.2 components, using the reference signal 66 as a phase reference. In another embodiment, an air-core second coil 68 and associated sense resistor $R_B$ are fed similar to the measurement coil 62 and associated sense resistor $R_A$ so as to provide for compensating for ambient temperature variations, wherein the first 62 and second 68 coils are similarly constructed. The measurement coil 62 can be oriented as illustrated in FIG. 6a to accommodate a bolt 12.1 with the head 12.11 above the shank 12.12 relative to the track surface 14, or as illustrated in FIG. 6b to accommodate a bolt 12.1 with the head 12.11 below the shank 12.12 relative to the track surface 14. In another embodiment, the first 20 and second 22 coils of the measurement coil pair 24 are oriented relative to the track surface 14 in accordance with the arrangement illustrated in FIG. 6b. In yet another embodiment, the eddy current part inspection system 10 incorporates either a pair of coils 62 or a plurality of first 20 and second 22 coils, one of the pair oriented in accordance with the arrangement illustrated in FIG. 6a, and the other of the pair oriented in accordance with the arrangement illustrated in FIG. 6b, so as to accommodate parts 12 oriented in either associated orientation from the part feeder 58.

Figure 8:
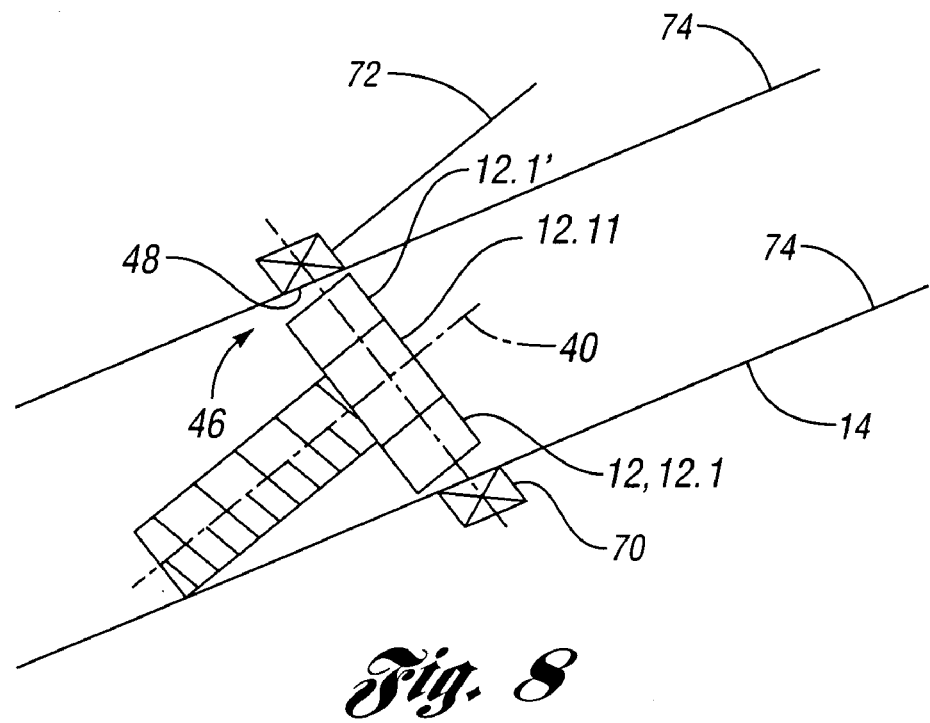
FIG. 8 illustrates a side cross-sectional view of a measurement coil of an eddy current part inspection system adapted for a hexagonal head bolt.
Figure 9:
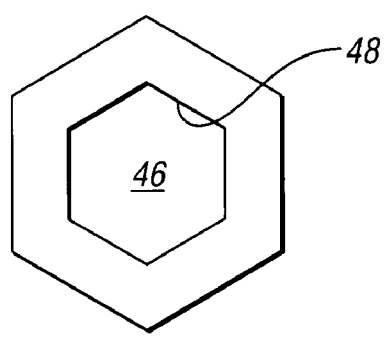
FIG. 9 illustrates a profile of the measurement coil of the eddy current part inspection system adapted for a hexagonal head bolt as illustrated in FIG. 8.

Referring to FIGS. 8 and 9, the core profile 48 of the measurement coil 62, or first 20 and second 22 coils, may be adapted to the profile of the part 12 being inspected as the part 12 slides through the measurement coil 62, or first 20 and second 22 coils. For example, for a hexagonal head bolt 12.1' illustrated in FIG. 8, the measurement coil 62, or first 20 and second 22 coils, may be shaped as illustrated in FIG. 9, to match the projection of the tilted head 12.11 on the tilted hexagonal head bolt 12.1', so that the profile of the tilted measurement coil 62, or first 20 and second 22 coils, substantially matches—with clearance—the tilted core profile 48 of the measurement coil 62, or first 20 and second 22 coils, as the hexagonal head bolt 12.1' slides through the measurement coil 62, or first 20 and second 22 coils. An elliptical or quasi-elliptical shaped core profile 48 can be used to accommodate a tilted circular head 12.11 of a bolt 12.1. Generally, the shape of the core profile 48 can be determined by projecting the profile of the tilted part 12 onto a coil form 70 that is tilted so that a normal 72 to the coil form 70 is parallel to a longitudinal axis 40 of the part 12, using projection lines 74 that are parallel to the track surface 14 and which bound the tilted part 12.

Referring to FIGS. 10a-c and 11, a portion 76 of the track 60 may be adapted to provide for integration of either a measurement coil pair 24 or a measurement coil 62 therewith. For example, in one embodiment, a block 78 of substantially non-magnetic and non-conductive material, e.g. DELRIN®, incorporates a longitudinal bore 80 therein, which functions as a track surface 14 to guide a part 12 therethrough. For example, with the block 78 and associated track surface 14 tilted at an angle α from horizontal, e.g. in accordance with the eddy current part inspection system 10 illustrated in FIG. 1, a part 12 fed into a first end 82 of the longitudinal bore 80 will slide therethrough and exit a second end 84 of the longitudinal bore 80, for example, onto another portion of the track 60 downstream of the block 78. For example, as a portion 76 of the track 60, the first end 82 of the longitudinal bore 80 cooperates with a part feeder 58 and possibly another portion of the track 60 so as to receive a part 12 therefrom, and the second end 84 of the longitudinal bore 80 cooperates with a remaining portion of the track 60 and an associated part sorter 38 so as to provide the inspected part 12 thereto. For example, the longitudinal bore 80 may be either machined or molded into block 78. Although a circular longitudinal bore 80' is illustrated, which can be readily dilled, milled, and/or reamed, other shapes may be utilized, for example, with a V-groove track surface 14, e.g. with a 90 or 120 degree angle, or a longitudinal bore 80 with a hexagonal cross-section, which can be formed by broaching or molding. Alternatively, the block 78 could be formed with a longitudinal channel instead of a longitudinal bore 80, although the closed form surrounding the longitudinal bore 80 provides for dimensional stability. The block 78 incorporates a groove 86 within which the measurement coil pair 24 or measurement coil 62 is wound, wherein the groove 86 is adapted so that the longitudinal magnetic field axis or axes 42, 44 of the measurement coil pair 24 or measurement coil 62 are skewed at the angle β relative to the track surface 14 so as to be substantially aligned with longitudinal axis 40 of a part 12 sliding on the track surface 14. For example, in one embodiment, the groove 86 is adapted to be substantially concentric with the portion of the part 12, e.g. the head 12.11 of a bolt 12.1, that is of greatest significance to the inspection process, when that portion of the part 12 is within the measurement coil pair 24 or measurement coil 62 along the longitudinal bore 80. In another embodiment, the groove 86 is adapted to be substantially concentric with the longitudinal bore 80. The top 78.1 and sides 78.2, 78.3 of the block 78 incorporate associated recesses 88.1, 88.2, 88.3 adapted to receive associated cover plates (not shown) which are fastened with associated screws (not shown) to the block 78 using associated threaded holes 90 therein, so as to provide access to and protection of the associated measurement coil pair 24 or measurement coil 62. The block 78 is also provided with associated threaded mounting holes 92 for attaching the block 78 to the associated hardware of the associated eddy current part inspection system 10. Furthermore, the block 78 incorporates first 94 and second 96 holes therethrough, the former upstream of the latter, and both aligned with the longitudinal bore 80, so as to provide for transmitting therethrough associated laser beams of associated first 16 and second 18 part detectors, the operation of which is described hereinabove.

Figure 14:
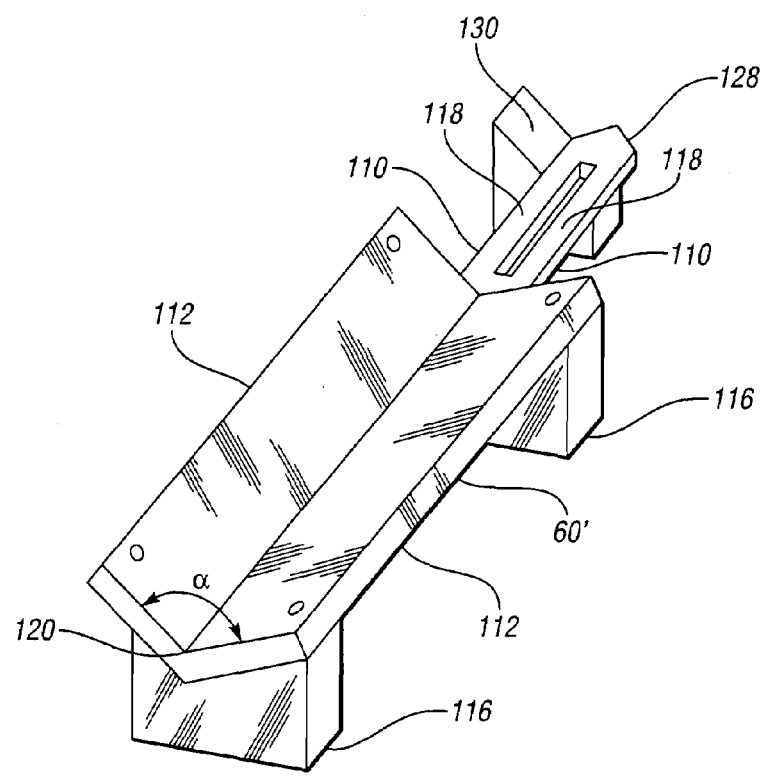
FIG. 14 illustrates a portion of the track assembly of the eddy current part inspection system illustrated in FIG. 12.
Figure 15A:
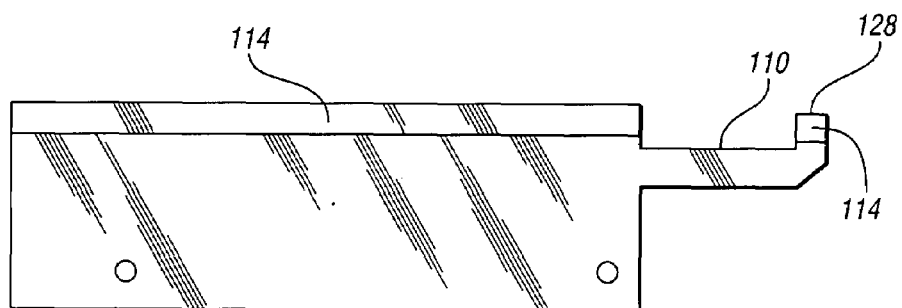
FIGS. 15a and 15b illustrate top and side views of a portion of a track element of the portion of the track assembly illustrated in FIG. 14.
Figure 15B:
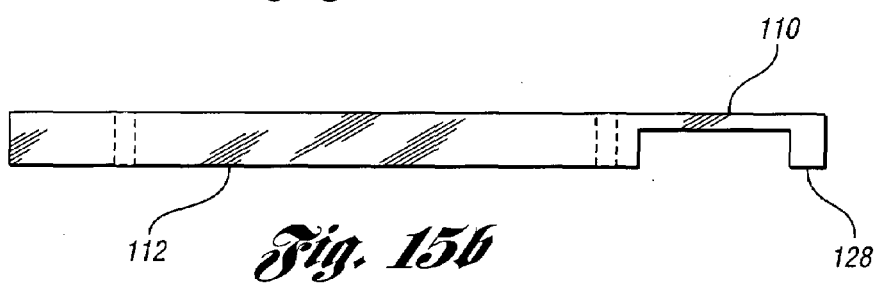
Figure 16:
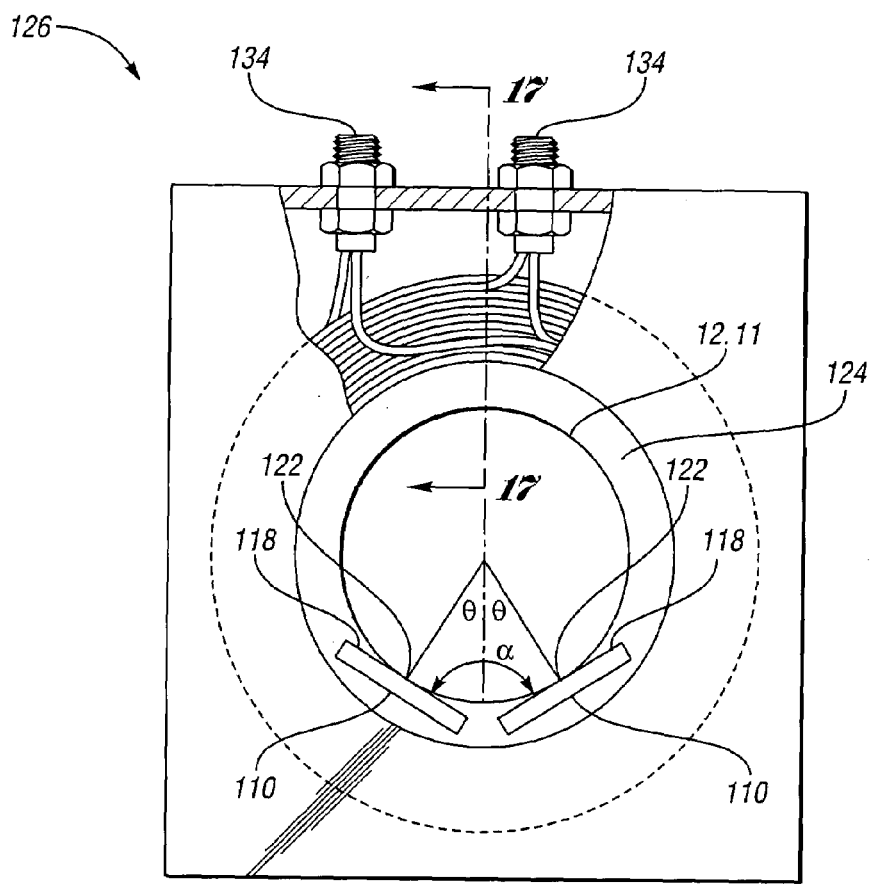
FIG. 16 illustrates a rear view of the eddy current sensor assembly illustrated in FIGS. 12 and 13, showing a cross-sectional view of a portion of the associated track assembly in cooperation therewith, and a fragmentary view of the associated coils.

Referring to FIGS. 12 and 13, a track and sensor assembly 98 of another embodiment of an eddy current part inspection system 10 comprises first 16 and second 18 part detectors, an eddy current sensor assembly 100, a track 60, third 102 and fourth 104 part detectors, and a part sorter 38, operatively coupled to a base plate 106. Also illustrated in FIG. 12 are a pair of pivot assemblies 108 used for attaching another part inspection apparatus (not shown). The track 60 comprises a V-groove track assembly 60' with a groove angle γ of about 120 degrees. The V-groove track assembly 60' comprises a plurality of track portions 60.1, one of which is illustrated in FIG. 14 which contains a reduced section 110 that extends through the eddy current sensor assembly 100 and provides for enabling a part 12 to be inspected to slide therethrough. Referring to FIGS. 14-16, the track portion 60.1 that extends through the eddy current sensor assembly 100 is, for example, constructed of a non-magnetic metallic material with good wear properties, for example, bronze. The track portion 60.1 comprises two plates 112 which mate with one another along corresponding chamfered edges 114, for example, with a chamfer angle of about 60 degrees so as to provide for the associated groove angle γ of about 120 degrees for the V-groove track assembly 60'. The plates 112 are fastened to stanchions 116, which are in turn fastened to the base plate 106. Referring to FIG. 16, the reduced section 110 of each plate 112 has a thickness of about 1 to 3 millimeters, and a width adapted so as to be wider than necessary to contact the part 12 on the face 118 of the reduced section 110, for example, for a circular head 12.11, about half again as wide as the distance from the internal apex 120 of the V-groove track assembly 60' to the point of tangency 122 where the head 12.11 contacts the face 118. The reduced sections 110 of both plates 112 extend through the opening 124 in the coil assembly 126. In one embodiment, the size of the opening 124 is about 25 percent larger than the diameter of the part 12. The opening 124, the reduced sections 110, and the locations thereof therein are adapted so that the portion of interest of the part 12 to be inspected, e.g. the head 12.11 of a bolt 12.1, is substantially concentric with the coil assembly 126 when located within the coil assembly 126 along the track 60. The reduced section 110 are formed as dado near the end 128 of the plate 112, wherein the end 128 hooks over and is supported by a third stanchion 130 attached to the base plate 106.

Figure 17:
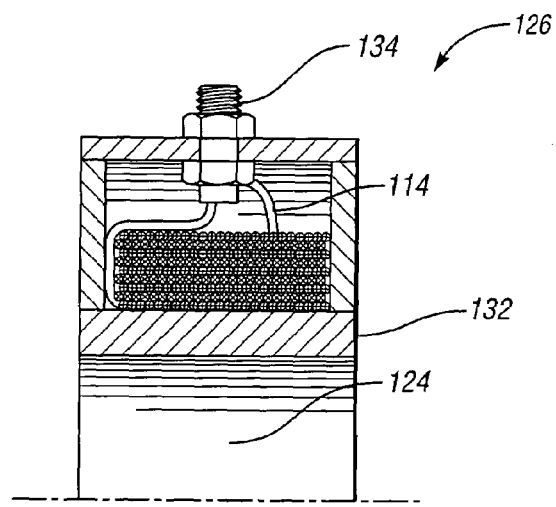
FIG. 17 illustrates a portion of a radial cross-section through the eddy current sensor assembly illustrated in FIG. 16.

Referring to FIGS. 16 and 17, the coil assembly 126 of an eddy current sensor assembly 100 comprises a spool 132, for example, constructed of DELRIN®, around which are wound the first 26 and second 30 coils of the measurement coil pair 24, or single measurement coil 62. For example, FIGS. 16 and 17 illustrate interleaved windings of the first 26 and second 30 coils of the measurement coil pair 24, each set of windings terminated in a corresponding electrical connector 134.

Figure 18A:
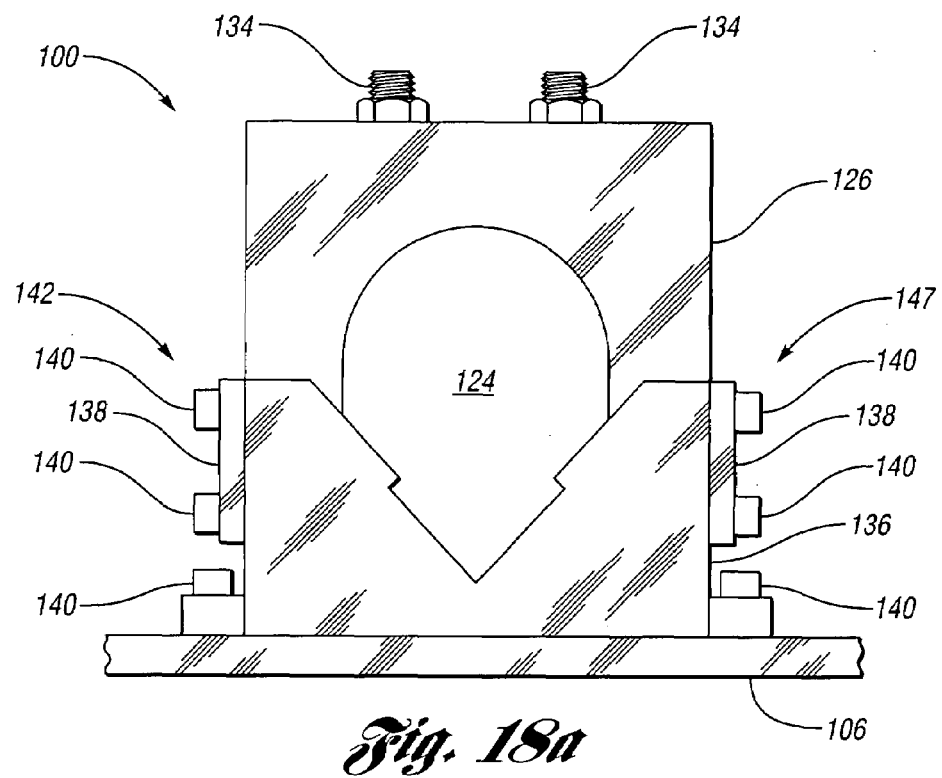
FIG. 18a illustrates a rear view of the eddy current sensor assembly illustrated in FIGS. 12 and 13, including the associated stanchion and support plates, with the associated track assembly removed.
Figure 18B:
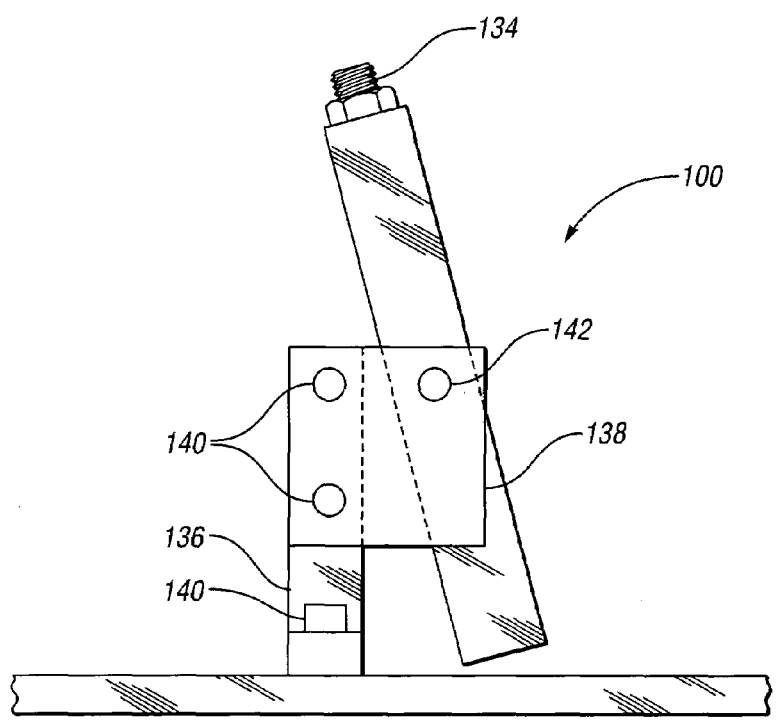

Referring to FIGS. 18a and b, the eddy current sensor assembly 100 comprises a coil assembly 126 attached to a stanchion 136 with a pair of hinge plates 138 attached with a plurality of fasteners 140 thereto. A pair of fasteners 142 connect through the hinge plates 138 to opposing sides of the coil assembly 126 so as to provide for pivoting the coil assembly 126 thereabout, so as to provide for aligning the coincident longitudinal magnetic field axes 42, 44 of the first 20 and second 22 coils with the longitudinal axis 40 of the part 12. The stanchion 136 is fastened to the base plate 106 with a plurality of fasteners 140.

Figure 19A:
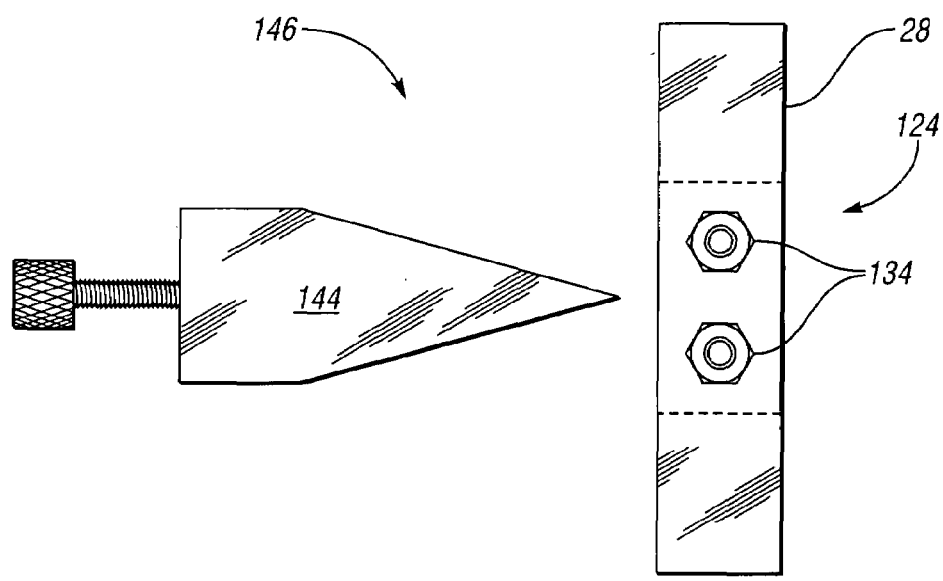
FIG. 19a illustrates a top view of a reference coil assembly in cooperation with an associated magnetic bias adjustment assembly.
Figure 19B:
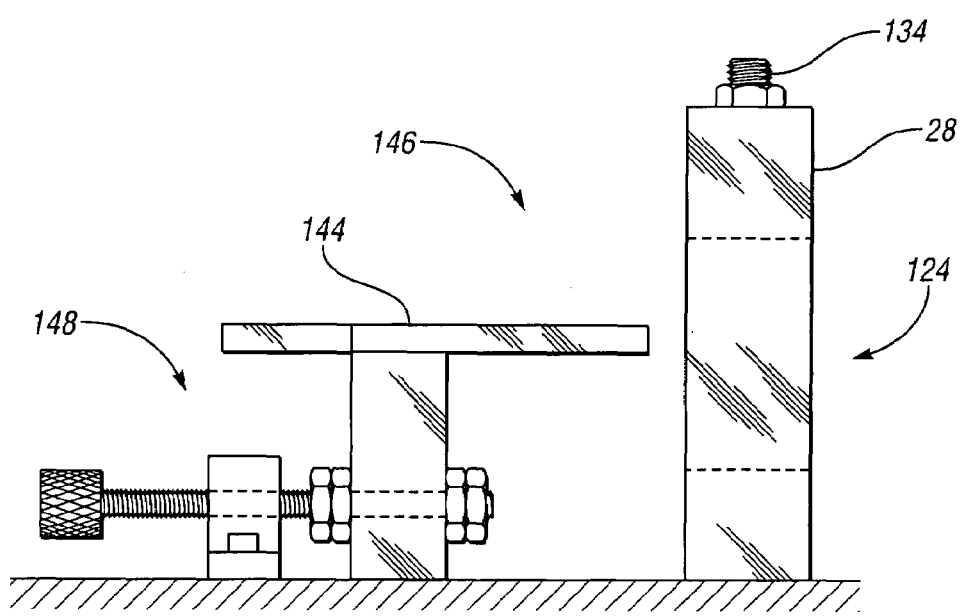

Referring to FIG. 19a-b, the metallic plates 112 used in the V-groove track assembly 60' can cause a bias to the associated measurement signal 50 as a result of eddy currents induced therein. The bias may be reduced or eliminated—thereby providing for improving the associated dynamic signal range of the measurement signal 50—by introducing a similar material perturbation to the associated reference coil pair 28, for example, with a tapered conductive element 144, e.g. constructed of a material similar to the track portion 60.1, e.g. bronze, as part of a magnetic bias adjustment assembly 146 which incorporates an adjustment mechanism 148 for adjusting the position of the tapered conductive element 144 relative to the reference coil pair 28.

While specific embodiments have been described in detail in the foregoing detailed description and illustrated in the accompanying drawings, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of any claims which are derivable from the description herein, and any and all equivalents thereof.

What is claimed is:

1. A part inspection system, comprising:
    a. at least one measurement coil adapted to generate a magnetic field responsive to a current in said at least one measurement coil, wherein said at least one measurement coil comprises:
        i. an opening adapted to receive a part to be inspected, wherein said part inspection system is adapted to provide for translating said part along a trajectory through said opening in said at least one measurement coil, said part to be inspected comprises a longitudinal axis, and said longitudinal axis of said part is skewed relative to said trajectory; and
        ii. a central longitudinal axis aligned with a nominal direction of said magnetic field within said opening of said at least one measurement coil, wherein said at least one measurement coil is skewed relative to said trajectory of said part so that said central longitudinal axis of said at least one measurement coil is substantially aligned with said longitudinal axis of said part.

2. A part inspection system as recited in claim 1, wherein said at least one measurement coil is adapted to be substantially concentric with said part when at least a portion of said part to be detected is within said opening of said at least one measurement coil.

3. A part inspection system as recited in claim 1, wherein said at least one measurement coil comprises first and second measurement coils, said first and second measurement coils respectively comprise first and second longitudinal axes respectively, said first and second longitudinal axes are aligned substantially parallel to one another, and both said first and second longitudinal axes are skewed relative to said trajectory so that each of said first and second longitudinal axes are substantially aligned with said longitudinal axis of said part to be inspected.

4. A part inspection system as recited in claim 3, wherein said first and second measurement coils are interleaved on a common spool.

5. A part inspection system as recited in claim 1, wherein said at least one measurement coil comprises a single measurement coil adapted to provide for generating said magnetic field, and said single measurement coil provides for generating a signal responsive to an interaction of said magnetic field with said part.

6. A part inspection system as recited in claim 5, wherein said signal is responsive to a self-impedance of said single coil.

7. A part inspection system as recited in claim 5, wherein said signal is compared with a corresponding signal from a reference coil substantially isolated from said part.

8. A part inspection system as recited in claim 1, wherein said at least one measurement coil and said opening in said at least one measurement coil are shaped so as to substantially conform to a projected shape of said part along said trajectory through said at least one measurement coil.

9. A part inspection system as recited in claim 1, further comprising a track adapted to provide for receiving a part to be inspected, wherein said track provides for enabling said part to slide therealong, and a point on said part defines said trajectory as said part slides along said track.

10. A part inspection system as recited in claim 9, wherein said track is slanted so as to provide for said part to slide under an influence of gravity.

11. A part inspection system as recited in claim 9, wherein said trajectory is parallel to a surface of said track.

12. A part inspection system as recited in claim 9, wherein said part is shaped so that when said part slides on said track along said trajectory, said longitudinal axis of said part is skewed relative to said trajectory.

13. A part inspection system as recited in claim 9, wherein a reduced section of said track extends through said at least one measurement coil.

14. A part inspection system as recited in claim 9, wherein said at least one measurement coil is integrated with at least a portion of said track.

15. A part inspection system as recited in claim 14, wherein a portion of said track is incorporated in a block of material, and said block of material incorporates a groove within which said at least one measurement coil is wound.

16. A part inspection system as recited in claim 1, further comprising a signal source operatively coupled to said at least one measurement coil so as to provide for causing a current to flow therethrough.

17. A part inspection system as recited in claim 16, wherein said signal source comprises a sinusoidal oscillator.

18. A part inspection system as recited in claim 3, further comprising first and second reference coils and a signal source, wherein said first and second reference coils are substantially isolated from influence by said part, said first reference coil and said first measurement coil are connected in series with said signal source, and said second reference coil is connected in a series combination with said second measurement coil with opposing phase.

19. A part inspection system as recited in claim 9, further comprising at least one part detector along said track, so as to provide for triggering at least one of a calibration process and a measurement process.

20. A part inspection system as recited in claim 19, wherein said at least one part detector comprises a light beam across a path of said part along said track.

21. A part inspection system as recited in claim 1, further comprising a processor adapted to generate a signal indicative of a condition of said part responsive to a signal from at least said at least one measurement coil.

22. A part inspection system as recited in claim 21, further comprising a part sorter adapted to either accept or reject said part responsive to a signal from said processor.

23. A part inspection system as recited in claim 1, further comprising a part feeder adapted to provide for repetitively feeding a plurality of said parts through said at least one measurement coil.

24. A method of inspecting a part, comprising:
　a. translating a part to be inspected along a trajectory, wherein a longitudinal axis of said part is skewed relative to said trajectory;
　b. generating a magnetic field along a longitudinal magnetic field axis, wherein said longitudinal magnetic field axis is skewed relative to said trajectory and substantially aligned with said longitudinal axis of said part; and
　c. detecting a signal responsive to an interaction of said part with said magnetic field.

25. A method of providing for inspecting a part, comprising:
　a. providing for translating a part to be inspected along a trajectory, wherein a longitudinal axis of said part is skewed relative to said trajectory;
　b. providing for generating a magnetic field along a longitudinal magnetic field axis, wherein said longitudinal magnetic field axis is skewed relative to said trajectory and substantially aligned with said longitudinal axis of said part; and
　c. providing for detecting a signal responsive to an interaction of said part with said magnetic field.

26. A part inspection system as recited in claim 18, further comprising a magnetic field influencing element adapted to cooperate with first and second reference coils so as to provide of cancelling a bias signal under a quiescent operating condition.

* * * * *